United States Patent
Choudhary et al.

(10) Patent No.: US 6,933,397 B2
(45) Date of Patent: Aug. 23, 2005

(54) PROCESS FOR EPOXIDATION OF A LIQUID OLEFINIC ORGANIC COMPOUND USING A SUPPORTED NANO-GOLD CATALYST

(75) Inventors: Vasant R. Choudhary, Maharashtra (IN); Nilesh S. Patil, Maharashtra (IN); Balu S. Uphade, Maharashtra (IN); Prabhas Jana, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/665,356

(22) Filed: Sep. 22, 2003

(65) Prior Publication Data

US 2005/0065355 A1 Mar. 24, 2005

(51) Int. Cl.$^7$ ............................................. C07D 301/12
(52) U.S. Cl. ........................................................ 549/529
(58) Field of Search ............................... 549/529; 514/23

(56) References Cited

U.S. PATENT DOCUMENTS 4,197,161 A  *  4/1980  Friedrich et al.  ............. 201/31

* cited by examiner

Primary Examiner—Kamal A. Saeed
(74) Attorney, Agent, or Firm—NIxon & Vanderhye P.C.

(57) ABSTRACT

The present invention relates to a process for the liquid phase epoxidation of a normally liquid olefinic compound to corresponding organic epoxide compound using aqueous or anhydrous organic hydroperoxide as an oxidizing agent in the presence of a supported nano-gold catalysts at the effective organic hydroperoxide/olefinic compound mole ratio, catalyst/olefinic compound weight ratio and temperature to yield the epoxide.

11 Claims, No Drawings

PROCESS FOR EPOXIDATION OF A LIQUID OLEFINIC ORGANIC COMPOUND USING A SUPPORTED NANO-GOLD CATALYST

FIELD OF THE INVENTION

The present invention relates to a process for the liquid phase epoxidation of a liquid olefinic organic compound. The present invention particularly relates to a process for the liquid phase epoxidation of a liquid olefinic organic compound to the corresponding epoxide, using a reusable solid catalyst comprising nano-size gold particles.

The process of the invention used for the production of organic epoxides, which are fine chemicals and/or used as intermediates in the preparation of fine chemicals or speciality chemicals in perfumery, dyes, pharmaceutical and other chemical industries.

BACKGROUND OF THE INVENTION

Epoxides are a class of compounds containing an oxarine ring,

They are conventionally produced by epoxidation of olefinic compounds containing olefinic group, C═C. Processes for the epoxidation of liquid olefinic compounds, using both homogeneous and heterogeneous solid catalyst, have been described in the prior art.
Epoxidation of Liquid Olefinic Compounds Using Homogeneous Catalysts.

U.S. Pat. No. 4,864,041 (1989) discloses a process for the homogeneous epoxidation reaction of an olefinic organic substrate, using transition metal-substituted polyoxomatallate catalyst, the transition metal used was Co, Mn, Cu, Fe, or Cr. According to U.S. Pat. No. 5,155,241 (1992) styrene oxide is prepared by reacting styrene and hydrogen peroxide in biphasic liquid system in the presence of a bis (tri-n-alkyltinoxy) molybdic acid and an inorganic anion. Another U.S. Pat. No. 5,223,613 (1993) discloses an olefin epoxidation process in which an olifinically unsaturated substrate is converted with an oxidizing agent in the presence of a catalytic amount of a bimetallic complex, each of the two metallic elements of which is selected from V, Cr, Mn, Fe, Co, Ni, Cu, Mo, Ru, Rh, Pd, W, Re, Os, Ir, and Pt. Another U.S. Pat. No. 5,510,516 (1996) discloses a process for epoxidation of unsaturated acrylates by contacting it with hydrogen peroxide or organic peracids in the presence of alkali metal molybdates or tungstates or heteropolyacid.

In all the prior art processes, since the catalyst is dissolved in the reaction mixture, the separation of the catalyst is difficult and the catalyst can not be reused in the process. Because of this a lot of undesirable waste is produced and also the cost of epoxide production is high hence there is a need for developing a heterogeneous solid catalyst, which can be separated from the reaction mixture simply by filtration and also can be reused in the process for several times. A few processes utilizing heterogeneous solid catalysts for the epoxidation of olefinic organic compounds have also been described in the prior art.
Epoxidation of Liquid Olefinic Compounds Using Heterogeneous Solid Catalysts According to U.S. Pat. No. 5,319,114 (1994), olefins are converted to epoxides by reacting them with an organic peroxide in the presence of a heterogeneous catalysts comprised of a carbon molecular sieve containing transition metal from the group IVA, VA, VIA, and VIIA transition elements, such as Ti, W, Cr, V, Mo, Ni, or Re. However, there is always a high possibility of leaching out of transition metals from the solid catalyst during the epoxidation process, causing a loss of catalytic activity and/or selectivity and also making difficult the separation of the leached out components from the reaction mixture [Reference I. W. C. E. Arends and R. A. Sheldon, Applied Catalysis A: General. Volume 212, page 175–187, year 2001]

European patent 0568336A2 disclosed a process for producing an epoxide by contacting an olefin with hydrogen peroxide in the presence of a titanium silicate zeolite catalyst. A recent U.S. Pat. No. 6,194,591 (2001) also disclosed an olefin epoxidation process using a titanium zeolite catalyst modified with Pt, Pd, or Cu compound. However, since the titanium silicate zeolite catalysts are acidic in nature they also catalyse the epoxide isomerization and/or epoxide ring opening, thereby reducing the selectivity for the formation of epoxide in the epoxidation process over these catalysts. For example, the isomerization of styrene oxide over Ti containing zeolite catalyst is quite fast and hence phenyl acetaldehyde instead of styrene oxide is formed in the epoxidation reaction [European Patent 0,100,117A1 (1984); Z. Fu et al. Microporous and Mesoporous Materials, volume 29, page 351–359 and year 1999]. Because of the limitations of the solid catalysts used in the prior art processes, there is a practical need to develop a better solid catalyst having higher selectivity for epoxide in the epoxidation of styrene and other liquid olefinic compounds and also high catalytic activity.

U.S. Pat. No. 6,534,661 discloses a bimetallic, primarily Pt and Pd noble metals supported on titanium containing silica support for the epoxidation of organic compounds such as propylene using hydrogen and oxygen at elevated pressure of 500–2000 psig. In this disclosure, the presence of Pt, Pd and Ti is essential for the epoxidation to occur. In addition, the reaction is carried out in gas/liquid phase but at elevated pressures and the catalyst is prepared by impregnation of reduced Pd and Pt containing solution (by hydrogen) on the titanium containing zeolite support. After filtration of the impregnated mass and drying, it is further reduced in hydrogen at 250–300° C. for 10–20 hours. The process of this disclosure is expensive and complicated requiring heterogeneous deposition for formation of the catalyst, and elevated pressures during application for epoxidation.

OBJECTS OF THE INVENTION

The main object of this invention is to provide a liquid phase process for the epoxidation of normally liquid olefinic organic compounds to corresponding epoxides, using a novel solid catalyst, which has high activity and also high selectivity for the epoxide formation in the process.

Another object of the invention is to provide a liquid phase process for the epoxidation of normally liquid olefinic organic compounds to corresponding epoxides, using a novel solid catalyst, which is easily separable from the reaction mixture and also reusable in the process.

SUMMARY OF THE INVENTION

The present invention provides a process for the liquid phase epoxidation of a normally liquid olefinic organic compound (I) by an aqueous or anhydrous organic hydroperoxide (II), using a solid catalyst comprising nano-size gold particles (III), the process comprises:

i. contacting a liquid mixture comprising I and II with III in a stirred batch reactor;
ii. removing the catalyst from the reaction mixture; and separating the reaction products and unconverted reactants from the reaction mixture.

In one embodiment of the invention, the catalyst is recycled to the reactor.

In another embodiment of the invention, the mole ratio of organic hydroperoxide (II) to olefinic organic compound (I) is in the range from 0.1 to 10, the weight ratio of catalyst (III) to olefinic organic compound (I) is above 0.001, the reaction temperature is in the range of 25° C. to 250° C., and the reaction time is in the range from 0.1 h to 100 h.

In another embodiment of the invention, the liquid olefinic compound is selected from the group consisting of styrene, substituted styrene, cyclohexene, substituted cyclohexene, 1-octene, other linear or non-linear liquid olefins, norbornene, cyclopentene, cyclooctene, allyl chloride, allyl alcohol and vinyl cyclohexene.

In another embodiment of the invention, the mole ratio of organic hydroperoxide (II) to olefinic organic compound (I) is between 0.3 and 3.0.

In another embodiment of the invention, the weight ratio of catalyst (III) to olefinic organic compound (I) is between 0.01 and 0.5.

In another embodiment of the invention, the reaction temperature is between 50° C. and 150° C.

In another embodiment of the invention, the reaction period is between 1 and 30 h.

In another embodiment, the organic hydroperoxide is selected from the group consisting of tertiary butyl hydroperoxide, tertiary amyl hydroperoxide, cumene hydroperoxide, ethyl benzene hydroperoxide, cyclohexyl hydroperoxide and methyl cyclohexyl hydroperoxide.

In another embodiment of the invention, the catalyst comprises nano-gold supported on a metal oxide.

In another embodiment of the invention, the metal oxide is selected from the group consisting of MgO, CaO, BaO, SrO, $Yb_2O_3$, $TiO_2$, $ZrO_2$, $HfO_2$, $V_2O_5$, $CrO_3$, $MoO_3$, $WO_3$, $MnO_2$, $Fe_2O_3$, CoO, NiO, CuO, ZnO, CdO, $B_2O_3$, $Al_2O_3$, $Ga_2O_3$, $Eu_2O_3$, $Tl_2O$, $SiO_2$, $SnO_2$, $Sb_2O_3$ and $Bi_2O_3$.

In another embodiment of the invention, the concentration of gold in the solid catalyst is between 0.1 wt % and 10 wt %.

In another embodiment of the invention, the process of the invention is carried out in the presence of water or non-aqueous solvent selected from the group consisting of benzene, toluene, ethyl acetate, liquid alkanes.

DETAILED DESCRIPTION OF THE INVENTION

The main finding of this invention is that the solid catalyst of this invention has high activity and epoxide selectivity in the process of the invention. Because of the high activity of the catalyst of this invention, the time required for obtaining the conversion of the olefinic compound (I) of practical interest is shortened by about 20%.

Another important finding of this invention is that the solid catalyst of this invention can be easily removed from the reaction mixture, simply by filtration, and also it can be reused in the process of this invention repeatedly.

The present invention provides a process for the liquid phase epoxidation of a normally liquid olefinic organic compound (I) by aqueous or anhydrous organic hydroperoxide (II), using a solid catalyst comprising nano-size gold particles (III). The process comprises a simple contacting of a liquid mixture comprising I and II with III in a stirred batch reactor at the following reaction conditions: mole ratio of II to I in the range from 0.1 to 10, weight ratio of III to I above 0.001, reaction temperature in the range from 25° C. to 250° C., and reaction period in the range from 0.1 h to 100 h. The catalyst is then removed from the reaction mixture and the reaction products separated from the unconverted reactants. The catalyst can be reused for subsequent reaction batches.

In the process of the invention, the main product is the epoxide of the liquid olefinic organic compound (I) used in the process and the other products are aldehydes and carboxylic acids, produced from the non-selective oxidation of the olefinic compound and tertiary alcohol produced from the organic hydroperoxide.

A number of normally liquid olefinic organic compounds known in the prior art may be used, such as for example styrene, substituted styrenes, cyclohexene, substituted cyclohexenes, 1-octene and other linear or non-linear liquid olefins, norbornene, cyclopentene, cyclooctene, allyl chloride, allyl alcohol, vinyl cyclohexene and the like.

In the process of the invention an organic hydroperoxide (II) is used as an oxidizing agent. Examples of the organic hydroperoxides are tertiary butyl hydroperoxide, tertiary amyl hydroperoxide, cumene hydroperoxide, ethyl benzene hydroperoxide, cyclohexyl hydroperoxide, methyl cyclohexyl hydroperoxide and the like In the process of the invention, the solid catalyst (III) is a nano particle size gold deposited on a metal oxide. Examples of metal oxides used in the catalyst of this invention are, MgO, CaO, BaO, SrO, $Yb_2O_3$, rare earth oxides, $TiO_2$, $ZrO_2$, $HfO_2$, $V_2O_5$, $CrO_3$, $MoO_3$, $WO_3$, $MnO_2$, $Fe_2O_3$, CoO, NiO, CuO, ZnO, CdO, $B_2O_3$, $Al_2O_3$, $Ga_2O_3$, $Eu_2O_3$, $Tl_2O$, $SiO_2$, $SnO_2$, $Sb_2O_3$, $Bi_2O_3$ and the like.

The supported nano-gold catalyst of this invention is preferably prepared by depositing gold chloride or gold hydroxide by impregnation technique and also by homogeneous and non-homogeneous precipitation, in the presence of metal oxide, techniques known in the prior art. After depositing the gold compound on metal oxide, the resulting mass can be calcined to yield a supported nano-gold catalyst. The particle size of gold particles in the catalyst of this invention may be below 100 nano meter.

In the process of the invention, the preferred mole ratio of organic hydroperoxide (II) to olefinic organic compound (I) is between 0.3 and 3.0; the preferred weight ratio of catalyst (III) to olefinic organic compound (I) is between 0.01 and 0.5; the preferred reaction temperature is between 50° C. and 150° C.; the preferred reaction period is between 1.0 h and 30 h; the preferred organic hydroperoxide is tertiary butyl hydroperoxide or cumene hydroperoxide or tertiary amyl hydroperoxide; the preferred catalyst is nano-gold supported on metal oxide; the preferred catalyst is nano-gold supported on ytterbium oxide or calcium oxide; the preferred concentration of gold in the solid catalyst is between 0.1 wt % and 10 wt % and the preferred liquid olefinic compound is styrene or substituted styrene.

The process of this invention can be carried out in a stirred batch reactor, fitted with a reflux condenser known in the prior art for carrying out liquid phase reactions.

In the process of this invention, the role of the reflux condenser fitted with the reactor is to condense reactants and/or solvent, and to return them back to the reaction mixture.

In the process of this invention, a reaction pressure above atmospheric pressure may be used to allow the reaction to be carried out at temperature higher than the normal boiling point of the reactants and/or solvent, by increasing the boiling point of said reactants and/or solvent with increasing the reaction pressure.

In the process of this invention, liquid olefinic organic compound (I) and organic hydroperoxide (II) are reactants and are converted partly or completely to said products.

The process of this invention may be carried out in the presence of water or non-aqueous solvent, such as benzene, toluene, ethyl acetate, liquid alkanes, and the like.

In the process of this invention, organic hydroperoxide (II) may be aqueous or anhydrous, the anhydrous organic hydroperoxide may be prepared from the commercially available aqueous hydroperoxide by contacting the later with non-aqueous organic solvent and removing the separated water layer.

In the first step of the process of this invention, liquid olefinic organic compound (I) reacts with organic hydroperoxide (II) to yield corresponding epoxide and other products in the presence of the solid catalyst (III).

The role of the solid catalyst is to enhance rate of the epoxidation reaction and thereby to drastically reduce the time required for the reaction.

The catalyst (III) of the process of this invention is heterogeneous with respect to the liquid reaction mixture and can be removed from the reaction mixture easily, simply by the filtration and it may be reused repeatedly for the subsequent reaction batches.

The present invention is described with reference to the following examples illustrating the process of this invention for the liquid phase epoxidation of normally liquid organic olefinic compound by organic hydroperoxide, using said solid catalyst comprising nano-size gold particles. However, these examples are provided for illustrative purposes only and or not to be construed as limitations on scope of the process of this invention.

Definitions of Terms Used in the Examples

Conversion of reactant (%)=mole % of reactant converted in the process. Selectivity of product (%)=[(mole % of reactant converted to the particular product)÷(mole % of reactant converted to all the products)]×100. Abbreviation used: TBHP=tertiary butyl hydroperoxide; TAHP=tertiary amyl hydroperoxide; CHP=cumene hydroperoxide.

EXAMPLES 1–16

These examples illustrates the process of this invention for the liquid phase epoxidation of liquid olefinic compounds by different organic hydroperoxides to corresponding epoxides using a reusable solid catalyst, comprising nano-size gold particles, of this invention.

The process of this invention was carried out at atmospheric pressure by contacting the solid catalyst with a 15 cm$^3$ liquid reaction mixture containing a liquid olefinic compound (I) and an organic hydroperoxide, with aqueous or non-aqueous solvent in a stirred batch reactor (capacity: 25 cm$^3$) and fitted with a reflux condenser and mercury thermometer dipped in the reaction mixture, under vigorous stirring at the reaction conditions given in Table-1, and after the reaction, cooling the reaction mixture close to room temperature and then analysing the products and unconverted reactants present in the reaction mixture, after separating the solid catalyst from it by filtration, by a gas chromatograph with a flame ionization detector, using a SE 30 column and nitrogen as a carrier gas.

Results of the epoxidation of olefinic compound by the process of this invention at different process conditions and using different olefinic compounds, organic hydroperoxides and catalysts of this invention are presented as examples in Table-1.

The solid catalysts used in these examples were prepared by the procedure given below.

Au (6.7 wt %)/Yb$_2$O$_3$ catalyst was prepared as follows: A 0.32 g HAuCl$_4$.3H$_2$O and 5.19 g extra-pure (NH$_2$CONH$_2$) were dissolved in 300 ml distilled water and to this solution 2.0 g Yb$_2$O$_3$ was added. The resulting mixture was heated slowly to 95±5° C. under continuous stirring and maintained at 95±5° C. for 6 h, while maintaining the pH and the temperature throughout the experiment, aged overnight at 30±5° C. The resulting solid was filtered, washed with 4 liter of distilled water, dried in air at 100° C. for 15 h and then calcined in air at 400° C. for 2 h to yield the catalyst. The surface area of the catalyst was 26.4 m$^2$g$^{-1}$ and the actual gold loading measured by ICP-OES on the support, Yb$_2$O$_3$ was 6.7 wt %. The particle size of the gold present in the catalyst was 5–8 nm. The surface area of the catalyst was measured by single point BET method. The gold loading was determined by the ICP-OES technique. The gold particle size was determined by transmission electron microscopy of the catalyst.

Au (4.7 wt %)/CaO catalyst was prepared by the procedure same as that used for the preparation of the Au (6.7%)/Yb$_2$O$_3$ catalyst except that CaO was used instead of Yb$_2$O$_3$. The surface area, gold loading and gold particle size of the catalyst were 19 m$^2$g$^{-1}$, 4.7 wt %, and 3–7 nm, respectively.

Au (6.0 wt %)/TiO$_2$ catalyst was prepared by the procedure same as that used for the preparation of the Au (6.7%)/Yb$_2$O$_3$ catalyst except that TiO$_2$ was used instead of Yb$_2$O$_3$. The surface area, gold loading and gold particle size of the catalyst were 15.5 m$^2$g$^{-1}$, 6.0 wt %, and 3–6 nm, respectively.

Au (7.5 wt %)/MgO catalyst was prepared by the procedure same as that used for the preparation of the Au (6.7%)/Yb$_2$O$_3$ catalyst except that MgO was used instead of Yb$_2$O$_3$. The surface area, gold loading and gold particle size of the catalyst were 24.5 m$^2$g$^{-1}$, 7.5 wt %, and 4–6 nm, respectively.

Au (8.5 wt %)/Tl$_2$O catalyst was prepared by the procedure same as that used for the preparation of the Au (6.7%)/Yb$_2$O$_3$ catalyst except that Tl$_2$O was used instead of Yb$_2$O$_3$. The surface area, gold loading and gold particle size of the catalyst were 9.2 m$^2$g$^{-1}$, 8.5 wt %, and 4–8 nm, respectively.

Au (6.5 wt %)/La$_2$O$_3$ catalyst was prepared by the procedure same as that used for the preparation of the Au (6.7%)/Yb$_2$O$_3$ catalyst except that La$_2$O$_3$ was used instead of Yb$_2$O$_3$. The surface area, gold loading and gold particle size of the catalyst were 81 m$^2$g$^{-1}$, 6.5 wt %, and 2–6 nm, respectively.

Au (6.8 wt %)/CuO catalyst was prepared by the procedure same as that used for the preparation of the Au (6.7%)/Yb$_2$O$_3$ catalyst except that CuO was used instead of Yb$_2$O$_3$. The surface area, gold loading and gold particle size of the catalyst were 19.3 m$^2$g$^{-1}$, 6.8 wt %, and 5–8 nm, respectively.

Au (0.7 wt %)/TiO$_2$ catalyst was prepared by the procedure same as that used for the preparation of the Au (6.0%)/TiO$_2$ catalyst except that 0.0425 g HAuCl$_4$.3H$_2$O was used instead of 0.32 HAuCl$_4$.3H$_2$O. The surface area, gold loading and gold particle size of the catalyst were 34.1 m$^2$g$^{-1}$, 0.7 wt %, and 2–4 nm, respectively.

Au (0.3 wt %)/MgO catalyst was prepared by the procedure same as that used for the preparation of the Au (7.5%)/MgO catalyst except that 0.012 g HAuCl$_4$.3H$_2$O was used instead of 0.32 HAuCl$_4$.3H$_2$O. The surface area, gold loading and gold particle size of the catalyst were 80.5 m$^2$g$^{-1}$, 0.3 wt %, and 2.5–5.0 nm, respectively.

TABLE 1

Results of the epoxidation of different olefinic compounds

|  | Example No. | | | |
| --- | --- | --- | --- | --- |
|  | Example-1 | Example-2 | Example-3 | Example-4 |
| Catalyst (III) | Au (6.7 wt %)/ $Yb_2O_3$ | Au (6.7 wt %)/ $Yb_2O_3$ | Au (6.7 wt %)/ $Yb_2O_3$ | Au (6.7 wt %)/ $Yb_2O_3$ |
| Reactants |  |  |  |  |
| Olefinic compound (I) | Styrene | Cyclohexene | 1-Octene | Styrene |
| Organic hydroperoxide (II) | Aqueous TBHP (70 wt % TBHP in water) | Aqueous TBHP (70 wt % TBHP in water) | Aqueous TBHP (70 wt % TBHP in water) | Anhydrous TBHP (26 wt % TBHP in benzene) |
| Reaction conditions |  |  |  |  |
| II/I mole ratio | 1.5 | 1.5 | 1.6 | 1.5 |
| III/I weight ratio | 0.08 | 0.09 | 0.08 | 0.1 |
| Temperature (° C.) | 85 | 80 | 85 | 80 |
| Reaction time (h) | 3.0 | 3.0 | 3.0 | 3.0 |
| Conversion of olefinic compound (I) (%) | 81.5 | 47.5 | 43.4 | 69.3 |
| Conversion of organic hydroperoxide (II) (%) | 69.3 | 32.6 | 39.1 | 48.1 |
| Main product of the reaction | Styrene oxide | Cyclohexene oxide | Epoxy octane | Styrene oxide |
| Selectivity for the main product (%) | 79.7 | 52.3 | 57.3 | 64.8 |

|  | Example No. | | | |
| --- | --- | --- | --- | --- |
|  | Example-5 | Example-6 | Example-7 | Example-8 |
| Catalyst (III) | Au (4.7 wt %)/ CaO | Au (6.0 wt %)/ $TiO_2$ | Au (7.5 wt %)/ MgO | Au (8.5 wt %)/ $Ti_2O$ |
| Reactants |  |  |  |  |
| Olefinic compound (I) | Styrene | Styrene | Styrene | Styrene |
| Organic hydroperoxide (II) | Anhydrous TBHP (26 wt % TBHP in benzene) | Anhydrous TBHP (26 wt % TBHP in benzene) | Anhydrous TBHP (26 wt % TBHP in benzene) | Anhydrous TBHP (26 wt % TBHP in benzene) |
| Reaction conditions |  |  |  |  |
| II/I mole ratio | 1.5 | 1.5 | 1.5 | 1.5 |
| III/I weight ratio | 0.08 | 0.08 | 0.08 | 0.08 |
| Temperature (° C.) | 80 | 80 | 80 | 80 |
| Reaction time (h) | 3.0 | 3.0 | 3.0 | 3.0 |
| Conversion of olefinic compound (I) (%) | 63.6 | 70.7 | 72.0 | 73.3 |
| Conversion of organic hydroperoxide (II) (%) | 36.2 | 95.6 | 82.0 | 49.1 |
| Main product of the reaction | Styrene oxide | Styrene oxide | Styrene oxide | Styrene oxide |
| Selectivity for the main product (%) | 70.1 | 52.0 | 54.5 | 58.9 |

|  | Example No. | | | |
| --- | --- | --- | --- | --- |
|  | Example-9 | Example-10 | Example-11 | Example-12 |
| Catalyst (III) | Au (6.5 wt %)/ $La_2O_3$ | Au (6.8 wt %)/ CuO | Au (0.7 wt %)/ $TiO_2$ | Au (0.3 wt %)/ MgO |
| Reactants |  |  |  |  |
| Olefinic compound (I) | Styrene | Styrene | Styrene | Styrene |
| Organic hydroperoxide (II) | Anhydrous TBHP (26 wt % TBHP in benzene) | Anhydrous TBHP (26 wt % TBHP in benzene) | Anhydrous TBHP (26 wt % TBHP in benzene) | Anhydrous TBHP (30 wt % TBHP in EtAc) |
| Reaction conditions |  |  |  |  |
| II/I mole ratio | 1.5 | 1.5 | 2.5 | 1.0 |
| III/I weight ratio | 0.08 | 0.08 | 1.0 | 0.01 |
| Temperature (° C.) | 80 | 80 | 80 | 80 |
| Reaction time (h) | 3.0 | 3.0 | 1.0 | 20.0 |
| Conversion of olefinic compound (I) (%) | 58.2 | 66.3 | 47.4 | 39.4 |

TABLE 1-continued

Results of the epoxidation of different olefinic compounds

| Conversion of organic hydroperoxide (II) (%) | 91.0 | 48.1 | 13.5 | 52.6 |
|---|---|---|---|---|
| Main product of reaction | Styrene oxide | Styrene oxide | Styrene oxide | Styrene oxide |
| Selectivity for main product (%) | 51.8 | 57.3 | 51.5 | 51.3 |

| | Example No. | | | |
|---|---|---|---|---|
| | Example-13 | Example-14 | Example-15 | Example-16 |
| Catalyst (III) | Au (6.0 wt %)/ TiO$_2$ | Au (6.0 wt %)/ TiO$_2$ | Au (6.0 wt %)/ TiO$_2$ | Au (6.7 wt %)/ Yb$_2$O$_3$ |
| Reactants | | | | |
| Olefinic compound (I) | Styrene | Styrene | Styrene | Styrene |
| Organic hydroperoxide (II) | Anhydrous TBHP (26 wt % TBHP in benzene) | Anhydrous TBHP (26 wt % TBHP in benzene) | Anhydrous TAHP (35 wt % TAHP in toluene) | Anhydrous CHP (30 wt % CHP in xylene) |
| Reaction conditions | | | | |
| II/I mole ratio | 1.5 | 1.5 | 1.5 | 1.5 |
| III/I weight ratio | 0.09 | 0.08 | 0.12 | 0.2 |
| Temperature (° C.) | 60 | 80 | 102 | 140 |
| Reaction time (h) | 3.0 | 0.5 | 6.0 | 1.0 |
| Conversion of olefinic compound (I) (%) | 39.1 | 40.1 | 80.6 | 70.3 |
| Conversion of organic hydroperoxide (II) (%) | 32.4 | 34.4 | 57.3 | 50.8 |
| Main product of the reaction | Styrene oxide | Styrene oxide | Styrene oxide | Styrene oxide |
| Selectivity for the main product (%) | 39.9 | 35.2 | 73.5 | 50.5 |

TBHP = tertiary butyl hydroperoxide
TAHP = tertiary amyl hydroperoxide, CHP = cumene hydroperoxide

EXAMPLES-17–20

The examples illustrate the process of this invention, showing reusability of the catalyst used in the earlier examples for the liquid phase epoxidation of liquid olefinic compound by the process of this invention.

The process of this invention for the liquid phase epoxidation of olefinic compound using the catalyst which was already used in the earlier examples was carried out using the reactor and the procedure same as that described in examples 1–16, except that the used catalyst in the earlier example was washed before its use with benzene or the olefinic substrate or organic hydroperoxide, which is to be used as reactant in the subsequent example.

The results showing the reusability of the catalyst of this invention in the process of this invention are presented in Table-2. These examples clearly show that the catalyst of the process of this invention has excellent reusability and it can be reused repeatedly in the process of this invention.

TABLE 2

Results showing reusability of the catalyst of this invention for the process of this invention.

| Example No. | Example-17 | Example-18 | Example-19 | Example-20 |
|---|---|---|---|---|
| Catalyst (III) | The catalyst after its use in Example-4 | The catalyst after its use in Example-17 | The catalyst after its use in Example-18 | The catalyst after its use in Example-19 |
| Reactants | | | | |
| Olefinic compound (I) | Styrene | Styrene | Styrene | Styrene |
| Organic hydroperoxide (II) | Anhydrous TBHP (26 wt % TBHP in benzene) | Anhydrous TBHP (26 wt % TBHP in benzene) | Anhydrous TBHP (26 wt % TBHP in benzene) | Anhydrous TBHP (26 wt % TBHP in benzene) |
| Reaction conditions | | | | |
| II/I mole ratio | 1.5 | 1.5 | 1.5 | 1.5 |
| III/I weight ratio | 0.09 | 0.08 | 0.07 | 0.06 |
| Temperature (° C.) | 80 | 80 | 80 | 80 |

TABLE 2-continued

Results showing reusability of the catalyst of this invention for the process of this invention.

| Example No. | Example-17 | Example-18 | Example-19 | Example-20 |
|---|---|---|---|---|
| Reaction time (h) | 3.0 | 3.0 | 5.0 | 8.0 |
| Conversion of olefinic compound (I) (%) | 66.3 | 63.1 | 71.5 | 72.2 |
| Conversion of organic hydroperoxide (II) (%) | 46.2 | 41.2 | 48.9 | 51.3 |
| Main product of the reaction | Styrene oxide | Styrene oxide | Styrene oxide | Styrene oxide |
| Selectivity for the main product (%) | 65.9 | 64.9 | 66.1 | 65.9 |

The Novel Features and Advantages of the Process of this Invention over the Prior Art Processes are as Follows:

i) The process of this invention uses a novel solid catalyst comprising nano-size particle of gold and this catalyst shows both high activity and epoxide selectivity in the liquid phase epoxidation of liquid olefinic compounds.

ii) The catalyst of the process of this invention can be separated from the liquid reaction mixture easily, simply by filtration.

iii) The catalyst of the process of this invention can be reused repeatedly for the epoxidation of liquid olefinic compounds in the process of this invention without a significant loss of its activity and selectivity.

iv) Unlike the transition metal oxide-containing solid catalysts used in the prior art processes the active component of the catalyst of the process of this invention is not leached out during the epoxidation process.

We claim:

1. A process for the liquid phase epoxidation of a normally liquid olefinic organic compound (I) by an aqueous or anhydrous organic hydroperoxide (II), using a solid catalyst comprising nano-size gold particles (III), the process comprising contacting a liquid mixture comprising I and II with III in a stirred batch reactor and then removing the catalyst from the reaction mixture and separating the reaction products and unconverted reactants from the reaction mixture.

2. A process as claimed in claim 1 wherein the catalyst is recycled to the reactor.

3. A process as claimed in claim 1 wherein the mole ratio of organic hydroperoxide (II) to olefinic organic compound (I) is in the range from 0.1 to 10, the weight ratio of catalyst (III) to olefinic organic compound (I) is above 0.001, the reaction temperature is in the range of 25° C. to 250° C., and the reaction time is in the range from 0.1 h to 100 h.

4. A process as claimed in claim 1 wherein the liquid olefinic compound is selected from the group consisting of styrene, substituted styrene, cyclohexene, substituted cyclohexene, 1-octene, other linear or non-linear liquid olefins, norbornene, cyclopentene, cyclooctene, allyl chloride, allyl alcohol and vinyl cyclohexene.

5. A process as claimed in claim 3 wherein the mole ratio of organic hydroperoxide (II) to olefinic organic compound (I) is between 0.3 and 3.0.

6. A process as claimed in claim 3 wherein the weight ratio of catalyst (III) to olefinic organic compound (I) is between 0.01 and 0.5.

7. A process as claimed in claim 3 wherein the temperature is between 50 C. and 150° C.

8. A process as claimed in claim 3 wherein the reaction period is between 1 and 30 h.

9. A process as claimed in claim 1 wherein the organic hydroperoxide is selected from the group consisting of tertiary butyl hydroperoxide, tertiary amyl hydroperoxide, cumene hydroperoxide, ethyl benzene hydroperoxide, cyclohexyl hydroperoxide and methyl cyclohexyl hydroperoxide.

10. A process as claimed in claim 1 wherein the catalyst comprises nano-gold supported on a metal oxide selected from the group consisting of MgO, CaO, BaO, SrO, $Yb_2O_3$, $TiO_2$, $ZrO_2$, $HfO_2$, $V_2O_5$, $CrO_3$, $MoO_3$, $WO_3$, $MnO_2$, $Fe_2O_3$, CoO, NiO, CuO, ZnO, CdO, $B_2O_3$, $Al_2O_3$, $Ga_2O_3$, $Eu_2O_3$, $Tl_2O$, $SiO_2$, $SnO_2$, $Sb_2O_3$ and $Bi_2O_3$.

11. A process as claimed in claim 10 wherein the concentration of gold in the solid catalyst is between 0.1 wt % and 10 wt %.

* * * * *